United States Patent [19]

Lenz et al.

[11] Patent Number: 5,573,918
[45] Date of Patent: Nov. 12, 1996

[54] PROCESS AND REAGENT FOR SPECIFIC DETERMINATION OF PANCREATIC ALPHA AMYLASE

[75] Inventors: Helmut Lenz, Tutzing; Martin Gerber, Weilheim-Unterhausen; Winfried Albert, Pähl, all of Germany

[73] Assignee: Boehringer Mannheim GmbH, Mannheim-Waldhof, Germany

[21] Appl. No.: 762,646

[22] Filed: Sep. 19, 1991

Related U.S. Application Data

[63] Continuation of Ser. No. 657,607, Feb. 19, 1991, abandoned, which is a continuation of Ser. No. 556,871, Jul. 20, 1990, abandoned, which is a continuation of Ser. No. 886,240, Jul. 16, 1986, abandoned.

[30] Foreign Application Priority Data

Jul. 19, 1985 [DE] Germany ............... 35 25 926.4

[51] Int. Cl.$^6$ .................. G01N 33/573; C07K 16/40
[52] U.S. Cl. ............. 435/7.4; 435/70.21; 435/172.2; 435/240.27; 435/810; 436/548; 530/388.26; 935/110
[58] Field of Search ...................... 435/7.1, 7.4, 22, 435/172.2, 240.27, 810; 70.21; 436/548; 530/387, 388.26; 935/110

[56] References Cited

FOREIGN PATENT DOCUMENTS

| 550266 | 3/1986 | Australia . |
|---|---|---|
| 3342736 | 6/1985 | Germany . |
| 8304312 | 12/1983 | WIPO . |

Primary Examiner—Christine M. Nucker
Assistant Examiner—Laurie Scheiner
Attorney, Agent, or Firm—Felfe & Lynch

[57] ABSTRACT

The present invention provides a process for the specific determination of pancreatic alpha-amylase in the presence of salivary alpha-amylase in body fluids, especially in serum, plasma, duodenal juice or urine, by reaction with a system for the detection of alpha-amylase in the presence of a monoclonal antibody which inhibits salivary alpha-amylase wherein, as inhibitor, there is used a first monoclonal antibody which specifically inhibits the salivary enzyme by less than 97%, in combination with a second monoclonal anti-saliva alpha-amylase antibody which inhibits this enzyme by less than 10%.

The present invention also provides a reagent for the specific determination of pancreatic alpha-amylase in the presence of salivary alpha-amylase in body fluids, especially in serum, duodenal juice, plasma or urine, containing a system for the detection of alpha-amylase and a monoclonal antibody against salivary alpha-amylase wherein it contains a first monoclonal antibody which specifically inhibits the salivary enzyme by less than 97%, in combination with a second monoclonal anti-salivary alpha-amylase antibody which inhibits this enzyme by less than 10%.

18 Claims, 1 Drawing Sheet

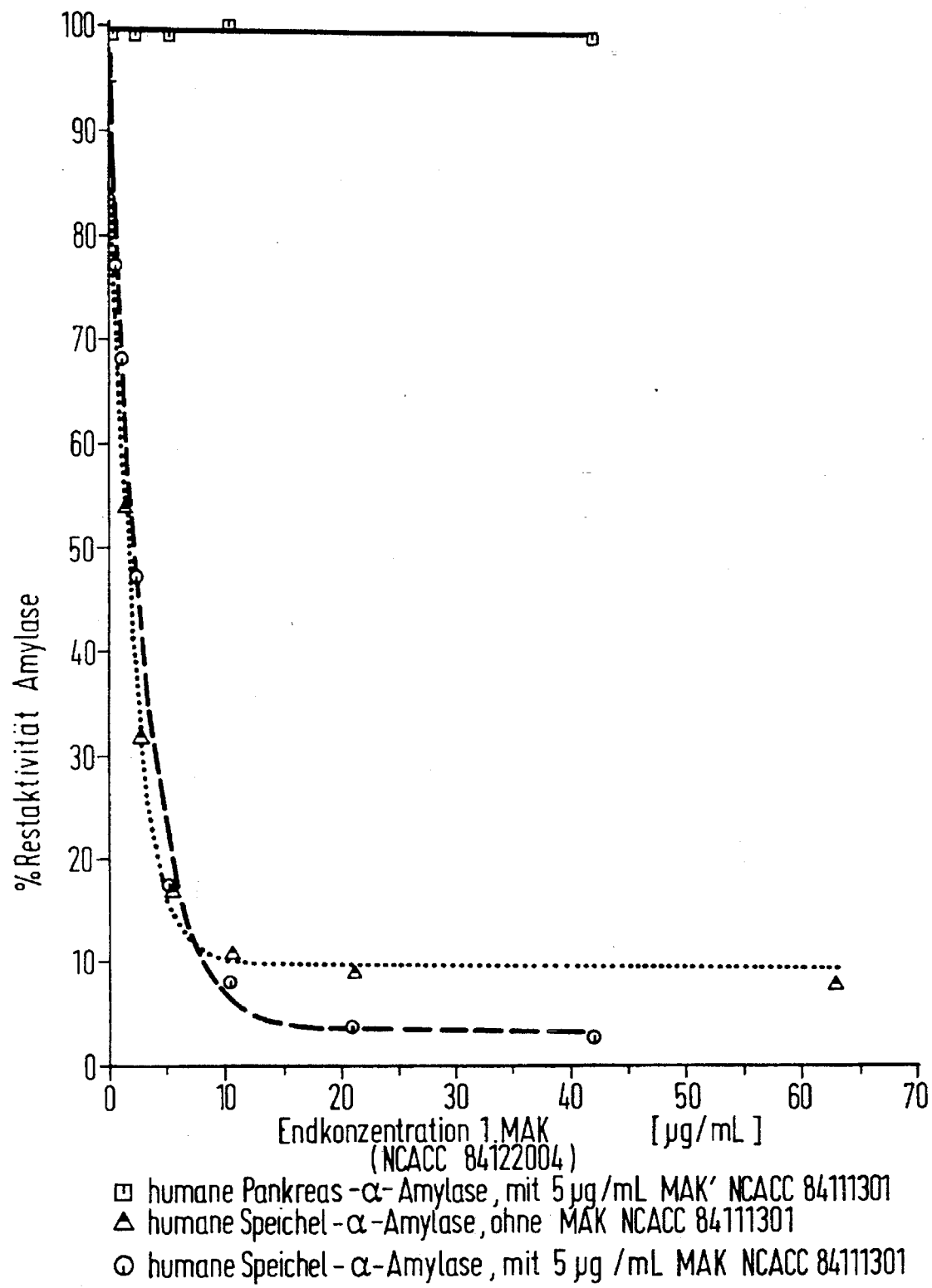

PROCESS AND REAGENT FOR SPECIFIC DETERMINATION OF PANCREATIC ALPHA AMYLASE

This application is a continuation of application Ser. No. 657,607, filed Feb. 19, 1991, now abandoned, which is a continuation of application Ser. No. 556,871, filed Jul. 20, 1990, now abandoned, which is a continuation of application Ser. No. 886,240, filed Jul. 16, 1986, now abandoned.

The present invention is concerned with a process and reagent for the specific determination of pancreatic alpha-amylase (h-PA) in the presence of salivary alpha-amylase (h-SA).

Alpha-amylase (E.C. 3.2.1.1 ) breaks down 1,4-alpha-glucosidically linked oligo- and polysaccharides preponderantly by random hydrolysis of the 1,4-alpha-glucosidic bonds to give maltose and malto-oligosaccharides. Besides industrial fermentation technology, the enzyme has considerable importance in the field of clinical analysis and diagnosis. Thus, in the case of numerous diseases, the alpha-amylase content in body fluids, such as serum, urine or duodenal secretion, changes considerably. However, in the body, essentially two alpha-amylase enzymes occur, the pancreatic enzyme and the salivary enzyme. Since diagnostic importance is only attributed to the pancreatic enzyme, the problem exists of analytically differentiating these two alpha-amylases in the presence of further isoenzymes occurring rarely and only in small amounts. The difficulty is that the two forms have a similar construction and are immunologically identical (K. Loreritz, Laboratoriumsblatter, 32, 118/1982 ). For the elimination of the activity of the salivary enzyme, it is known to employ adsorption on anion exchangers, inhibition by wheat protein, electrophoresis or electrofocussing. However, these processes are either unsatisfactory in their separating action or are too laborious for routine diagnosis. Amongst the mentioned methods, only the process described in Clin. Chem., 23/7, 1525–1527/1982 of inhibiting the enzyme of the salivary type by an inhibitor obtained from wheat germs involves a time expenditure acceptable for routine diagnosis, but its selectivity is unsatisfactory. In addition, in the case of the optimum inhibitor concentration, about 13% of the activity of the salivary type enzyme is maintained, whereas the activity of the pancreatic enzyme is reduced to about 81%.

In European Patent koplication No. 84 114 172.4, it has already been suggested to determine pancreatic alpha-amylase in the presence of salivary alpha-amylase by working in the presence of a monoclonal antibody which reacts with salivary alpha-amylase and displays a cross-reactivity of 5% or less towards pancreatic alpha-amylase. With this monoclonal antibody, it is also possible, in the case of the addition of a precipitating agent, to form an insoluble complex with salivary alpha-amylase which can be separated from the solution so that only the pancreatic enzyme remains behind in the solution and can then determined. Alternatively, it is possible to use the monoclonal antibody in immobilized form and, in this way, to separate off the salivary amylase. However, in both cases, it is necessary to form an insoluble phase and to separate it from the soluble phase.

German patent application DE A-1 35 00 526.2, discloses a process of the described kind in which, instead of the binding monoclonal antibody of the above-mentioned European Patent Application, there is used a monoclonal antibody which specifically inhibits the salivary isoenzyme. A further improvement of the alpha-amylase isoenzyme determination is achieved without having to carry out a phase separation but the maximum achieved inhibition of the salivary enzyme is less than 97% so that there is still an undesirably large inexactitude of the determination.

Therefore, it is an object of the present invention to overcome this disadvantage and to provide a process and a reagent which make possible a quick and simple but more exact determination of pancreatic alpha-amylase in the presence of alpha-amylase of the salivary type in body fluids.

Thus, according to the present invention, there is provided a process for the specific determination of pancreatic alpha-amylase in the presence of salivary alpha-amylase in body fluids, especially in serum, plasma, duodenal juice or urine, by reaction with a system for the detection of alpha-amylase in the presence of a monoclonal antibody which inhibits the salivary alpha-amylase, wherein, as inhibitor, there is used a first monoclonal antibody which specifically inhibits the salivary enzyme by less than 97%, in combination with a second monoclonal anti-salivary alpha-amylase antibody which inhibits this enzyme by less than 10%.

Inhibiting antibodies with <93% inhibition are especially preferred for the present invention as first monoclonal antibody and binding antibodies with <5% inhibition of the salivary enzyme as second monoclonal antibody. The lower limiting value of the inhibition is to be regarded as being about 70% and preferably 80% in order to achieve an inhibition of over 97% in the combination according to the present invention.

The process according to the present invention is based upon the very surprising observation that the inhibiting effectiveness of a monoclonal antibody which does not fully satisfactorily inhibit the salivary enzyme is synergistically potentiated by an antibody which only binds to salivary alpha amylase but, for practical purposes does not completely or sufficiently inhibit the enzyme and almost quantitative inhibition of the salivary enzyme can be achieved with 100% maintenance of the activity of the pancreatic enzyme. Furthermore, it is possible to reduce the incubation time substantially.

For the process of the present invention, as first monoclonal antibodies there are preferably used the antibodies obtained from the cell cultures deposited with the NCACC under the numbers (99D12) 84122003 and (89E2) 84122004 (National Collection of Animal Cell Cultures, Porton Down, GB). As second monoclonal antibodies, there are preferably used the binding antibodies disclosed in EU-A1 84 114 172.4 of the cell cultures deposited with the NCACC under the numbers 84111301 and 84111302, NCACC 84111301 being especially preferred.

The particularly needed amount of first and second antibody can, for definite antibody preparations, easily be ascertained by a few preliminary experiments. It is preferable to use at least 5/µg./ml. and more preferably at least 20/µg./ml. of the first monoclonal antibody and at least 1 µg./ml. and more preferably at least 5/µg./ml. of the second monoclonal antibody.

Monoclonal antibodies which can be used according to the present invention can be obtained by immunized experimental animals with native or modified salivary alpha-amylase, fusing B-lymphocytes of the so obtained immunized animals with transforming agents, cloning and culturing the so formed hybrid cells which produce the monoclonal antibodies and isolating the latter. Especially preferred animals for producing the salivary alpha-amylase antibodies are rats and mice. The immunization takes place either with native human salivary alpha-amylase or with modified salivary amylase. If native enzyme is used, commercially available, electrophoretically homogeneous preparations can be used. Chemically modified salivary alpha-amylase can also be obtained according to known methods of enzyme modification, such as are described in more detail, for example, in DE-AS 25 43 994. Preferred modifying agents include, for example, N-bromosuccinimide (NBS) with oxidation of tryptophan groups on the protein (BBA, 143, 462–472/1967), carboxymethylation with iodoacetate (IAA), which mainly attacks on the histidine or nitration with tetranitromethane (TNM) (J. Biol. Chem., 238, 3307/1963), as well as diazotisation with diazotised sulphanilic acid (Meth. Enzymol., 25, 515–531/ 1972). As best suited, there thereby proves to be the enzyme modified with TNM in the case of the use of Balb/c mice or the native enzyme in the case of the use of AJ mice.

The immunization takes place by the usual administration of the native or modified enzyme, preferably in combination with adjuvant. As adjuvant, it is preferred to use aluminium hydroxide, together with *Bordatella pertussis*. If, for the immunization, there is used native salivary alpha-amylase in AJ mice or TNM-modified salivary alpha-amylase in Balb/c mice, then the immunization preferably takes place over the course of at least 9 months with at least 7 immunization (injections i.p.).

After immunization has taken place, the B-lymphocytes of the immunized animals are fused according to usual methods with transforming agents. Examples of transforming agents which can be used in the scope of the present invention include myeloma cells, transforming viruses, for example Epstein-Barr virus, or the agents described in published German Patent Specification No. 32 45 665. The fusion takes place according to the known process of Koehler and Milstein (Nature, 256 (1975) 495–497). The hybrid cells formed are cloned in the usual way, for example with the use of a commercially available cell sorter, and the clones obtained which form the desired monoclonal antibodies are cultured. On the basis of the cancer-like growth of the hybrid cells, these can be further cultured for an indefinite time and produce the desired monoclonal antibodies in any desired amount.

For the determination process according to the present invention, the monoclonal antibodies can be used as such or their fragments (Fab fragments) displaying corresponding immunological properties. Therefore, under the term "monoclonal antibodies" are here also understood the fragments. Not only the complete antibody but also its fragments can be used in immobilized form.

The determination of the alpha-amylase as such takes place according to known methods. Since the combination of monoclonal antibodies according to the present invention selectivity inhibits alpha-amylase of the salivary type and thus removes it from the enzyme activity determination without impairing the pancreatic enzyme the values obtained in the case of the alpha-amylase determination in the presence of the monoclonal antibody correspond solely to the activity due to the pancreatic enzyme.

The process according to the present invention is preferably carried out with a system for the detection of alpha-amylase which contains a maltopolyose with 4 to 7 glucose residues in the molecule, maltose phosphorylase, β-phosphoglucomutase, glucose-6-phosphate dehydrogenase and NAD.

A further system preferably used in the scope of the present invention for the detection of the alpha-amylase comprises nitrophenylmaltopolyose with 4 to 7 glucose residues in the molecule and alpha-glucosidase.

A further preferred detection system for alpha-amylase comprises starch modified with determinable groups. The term "modified starch" includes, for example, starch which is modified with determinable groups, for example the product of the firm Pharmazia, Sweden, commercially available as "Phadebas", as well as the product described in DE-OS 28 12 154, as well as starch changed in breakdown behaviour, for example carboxymethyl starch and boundary dextrins. All these systems are known and, therefore, do not require more detailed description.

For the carrying out of the process according to the present invention, the sample liquid is either first incubated with the antibodies used according to the present invention and thereafter used directly in a usual amylase test or a mixture of the antibodies with the amylase detection reagent without substrate is taken and, after the incubation, started by the addition of substrate. The period of the incubation time is dependent upon the activity of the antibodies used and is preferably 0.5 to 10 and especially about 5 minutes.

Insofar as a separation of the salivary alpha-amylase appears to be desirable, one of the monoclonal antibodies, not only in complete form but also in the form of fragments, can also be present fixed on to a solid carrier, for example on immunosorptive paper or on the surface of synthetic resin test tubes or tubes. In this way, the alpha-amylase of the salivary type is bound on to the carrier, i.e. on to the solid phase.

The following experiments confirm the effect achieved by the present invention:

Monoclonal antibodies (MAB) which inhibit h-SA specifically to a maximum of 93% are purified by ammonium sulphate precipitation and DEAE chromatography according to conventional methods. An MAB which specifically binds h-SA is also purified. The monoclonal antibody or antibodies in solution are premixed with human amylase and this mixture is incubated for 5 minutes at ambient temperature. Thereafter, this mixture is added to the amylase reagent and the amylase activity is measured. As control, there is used amylase premixed with buffer but without MAB's. Alternatively, the monoclonal antibody or antibodies is or are placed in a part of the amylase reagent—the alpha-glucosidase solution. Thereafter, the amylase solution is added thereto a followed by incubation for 5 minutes. The reaction is started with the substrate—$G_7PNP$ (p-nitrophenylmaltoheptaoside). As control solution, there is used a glucosidase solution without MAB's. FIG. 1 of the accompanying drawings shows the % residual activity of the h-SA or h-PA with and without binding MAB as a function of the end concentration of inhibiting MAB, determined by the substrate start method. The following Table 1 gives the results of the serum start method (MAB(s) and amylase premixed).

TABLE 1

Inhibition of human salivary and pancreatic alpha-amylase by inhibiting MAB NCACC 84122003 (MAB I) or 84122004 (MAB II) and/or binding MAB NCACC 84111301 (MAB III); serum start method, $G_7$PNP as substrate. TA = total activity, A = activity with MAB(s), RA = % residual activity

| alpha-amylase | TA (U/l) | MAB I 30 μg/ml | | MAB II 25 μg/ml | | MAB III 5 μg/ml | | MABs I/II 30/5 μg/ml | | MABs II/III 25/5 μg/ml | |
|---|---|---|---|---|---|---|---|---|---|---|---|
| | | A (U/l) | RA (%) | A (U/l) | RA (%) | A (U/l) | RA (%) | A (U/l) | RA (%) | A (U/l) | RA (%) |
| saliva | 1476 | 127 | 8.6 | 135 | 9.1 | 1430 | 96.9 | 40 | 2.7 | 37 | 2.5 |
| pancreatic | 1430 | 1442 | 100.8 | 1428 | 99.9 | 1424 | 99.6 | 1405 | 98.2 | 1426 | 99.7 |

On the basis of the Figure and of the Table, it is shown that the combination of inhibiting, specific MAB, as well as specific h-SA-binding MAB, brings about a synergistic increase of inhibition of salivary alpha amylase. This effect is independent of the substrate. It is also found in the case of high molecular weight substrates (colored starch), as well as in the case of short-chained substrates, for example $G_5$PNP (p-nitrophenylmaltopentaoside). The effect is also observed with the substrate eth-$G_7$PNP. Salivary alpha-amylase in human sera is also synergistically inhibited by the two MAB's.

The present invention also provides a reagent for the specific determination of pancreatic alpha-amylase in the presence of salivary alpha-amylase in body fluids, especially in serum, duodenal juice, plasma or urine, containing a system for the detection of alpha-amylase and a monoclonal antibody against salivary alpha-amylase wherein it contains s first monoclonal antibody which specifically inhibits the salivary, enzyme by less than 97%, in combination with a second monoclonal anti-salivary alpha-amylase antibody which inhibits this enzyme by less than 10%.

With regard to the system contained in the reagent according to the present invention for the detection of alpha-amylase and the other conditions, the above statements regarding the process apply correspondingly.

The present invention makes possible a simple quick and very precise determination of pancreatic alpha-amylase (h-PA) in the presence of alpha-amylase of the salivary type (h-SA) in body fluids and thus considerably improves the possibilities of clinical diagnosis.

The following Examples are given for the purpose of illustrating the present invention:

EXAMPLE 1

Inhibition of the human pancreatic and salivary alpha-amylase by 1st MAB (NCACC 84122004) alone and in combination with 2nd MAB (NCACC 84111301); serum start method:

Reagents: buffer: 100 mM $PO_4^{3-}$, 150 mM sodium chloride, 6% bovine serum albumin (pH 7.1)
amylase reagent: $G_7$PNP (Boehringer Mannheim (cat. order No. 568589, 37° C.)
MAB-1: 0.63 mg./ml. 1st MAB in buffer
MAB-2: 0.63 mg./ml. 1st MAB and 0.105 mg./ml. 2nd MAB in buffer
MAB-3: 0.105 mg./ml. 2nd MAB in buffer
h-SA: about 3000 U/l. ($G_7$PNP) in buffer
h-PA: about 3000 U/l. ($G_7$PNP) in buffer Experiment: 100 μl. h-SA or h-PA are, in each case, mixed with 100 μl. buffer or the various MAB solutions and incubated for 5 minutes at ambient temperature. Thereafter, in each case, 25 μl. of these mixtures are added to 1000 μl. of amylase reagent pre-tempered to 37° C. and the amylase activity is determined according to the manufactures instructions. The residual activity is calculated according to the following equation:

$$\text{residual activity (\%)} = \frac{\text{act. with } MAB(s)}{\text{act. without } MAB(s)} \times 100$$

Result: The corresponding residual activities of h-SA are, with 1st MAB, 8.6% and with 2nd MAB 96.9% and with both MAB's 2.7%. The h-PA residual activities are correspondingly 100 1% 99.6% and 99.7%.

EXAMPLE 2

Inhibition of the amylase by 1st MAB (NCACC 84122003) and/or 2nd MAB (NCACC 84111301): serum start version Reagents: as in Example 1 except that MAB-1 and MAB-2 are changed.
MAB-1': 0.525 mg./ml. 1st MAB in buffer
MAB-2': 0.525 mg./ml. 1st MAB and 0.105 mg./ml. 2nd MAB in buffer
Experiment: as in Example 1, as well as the calculation of the % residual activity
Result: The residual activities of h-SA are, with 1st MAB, 9.1%, with 2nd MAB 9.69% and with both MAB's 2.5%. The h-PA residual activities are correspondingly 99.9% 99.6% and 99.7%.

EXAMPLE 3

Inhibition of the human salivary and pancreatic alpha-amylase by 1st MAB (NCACC 34122004) with and without 2nd MAB (NCACC 84111301); substrate start method Reagents: buffer (as in Example 1)
h-SA (as in Example 1)
h-PA (as in Example 1)
MAB-1": 1st MAB in buffer, various concentrations
MAB-2": 2nd MAB in buffer, 0.513 mg./ml. alpha-glucosidase: from alpha-amylase reagent (Boehringer Mannheim, Cat. Order No. 568589) substrate: $G_7$PNP from alpha-amylase reagent Experiment: To 880 μl. alpha-glucosidase are added 10 μl. of an MAB-1" solution, as well as 10 μl. MAB-2" solution or 10 μl. buffer. 25 μl. h-PA or h-SA are mixed therewith. This mixture is incubated for 5 minutes at 37° C. Thereafter, the start takes place by the addition of 100 μl. substrate solution and the determination of the amylase activity after initiation. As control, there is used a mixture of alpha-glucosidase with 20 μl. buffer, as well as the corresponding alpha-amylase. The activity with MAB(s) divided by the activity without MAB's gives the % residual activity.

Results: FIG. 1 of the accompanying drawings shows the residual activity as a function of the end concentration of the 1st MAB in the case of h-SA with and without 2nd MAB and in the case of h-PA only with 2nd MAB.

We claim:

1. Method for the specific determination of pancreatic alpha amylase in the presence of salivary alpha-amylase in a body fluid sample comprising reacting said body fluid sample with a system for the detection of alpha-amylase and a monoclonal antibody reagent which inhibits salivary alpha amylase, wherein said monoclonal antibody reagent comprises a first monoclonal antibody which specifically inhibits the salivary alpha amylase by more than 70% and less than 93% and a second monoclonal anti-salivary alpha amylase antibody which inhibits salivary alpha amylase by less than 10% so as to inhibit said salivary alpha amylase and determining a reaction between said system and said alpha amylase, wherein reaction therebetween is indicative of pancreatic alpha amylase and not salivary alpha amylase.

2. Process according to claim 1, wherein the first antibody inhibits the salivary enzyme by less than 93% and the second antibody inhibits salivary alpha amylase by less than 5%.

3. Process according to claim 1, wherein said first and second monoclonal antibodies are obtained by immunizing AJ mice with native or modified salivary alpha amylase to provoke an immunological response thereto by B-lymphocytes of said AJ mice fusing said B-lymphocytes with a transforming agent, cloning and culturing said fused cells and isolating the monoclonal antibodies therefrom.

4. Method of claim 1, wherein the first monoclonal antibody is NCACC No. 84122003 or NCACC No. 84122004.

5. Method of claim 1, wherein the second monoclonal antibody is NCACC No. 84111301 or NACACC No. 84111302.

6. Method of claim 1 comprising using at least 5 ug/ml of said first monoclonal antibody and at least 1 ug/ml of said second monoclonal antibody.

7. Method of claim 6, comprising using at least 20 ug/ml of said first monoconal antibody and at least 5 ug/ml of said second monoclonal antibody.

8. Method of claim 1, wherein said system for the detection of pancreatic alpha amylase is a maltopolyose with 4 to 7 glucose residues, maltose phosphorylase, B-phosphoglucomutase, glucose-6-phosphate dehydrogenase and NAD.

9. Method of claim 1, wherein said system for the detection of pancreatic alpha amylase is a nitrophenylmaltopolyose having 4 to 7 glucose units together with alpha glucosidase.

10. Method of claim 1, wherein said system for the detection of alpha amylase is starch which has been modified with a determinable group.

11. Reagent for the specific determination of pancreatic alpha amylase in the presence of salivary alpha amylase in a body fluid sample comprising a system for the detection of alpha amylase a first monoclonal antibody against salivary alpha- amylase which specifically inhibits salivary alpha amylase by more than 70% and less than 93% and a second monoclonal anti-salivary alpha-amylase antibody which inhibits salivary alpha-amylase by less than 10%.

12. Reagent according to claim 11, wherein said system for the detection of alpha-amylase comprises a maltopolyose having 4 to 7 glucose residues, maltose, phosphorylase, β-phosphoglucomutase, glucose 6-phosphate dehydrogenase and NAD.

13. Reagent according to claim 11, wherein said system for the detection of pancreatic alpha amylase comprises a nitrophenyl maltopolyose with 4 to 7 glucose units and alpha-glucosidase.

14. Reagent according to claim 11, wherein said system for the detection of alpha-amylase comprises starch modified with a determinable group.

15. Process as in claim 1, wherein said body fluid is selected from the group consisting of serum, plasma, duodenal fluid, and urine.

16. Reagent as in claim 11, wherein said first monoclonal antibody is selected from the group consisting of NCACC No. 84122003 and NCACC No. 84122004.

17. Reagent as in claim 11, wherein said second monoclonal antibody is selected from the group consisting of NCACC No. 84111301 and NCACC No. 84111302.

18. Reagent of claim 11, wherein said first antibody inhibits salivary alpha-amylase by less than 93% and said second antibody inhibits salivary amylase by less than 5%.

* * * * *